US009400766B2

(12) United States Patent
Chee et al.

(10) Patent No.: US 9,400,766 B2
(45) Date of Patent: Jul. 26, 2016

(54) DETERMINING COMBINATIONS OF ODORS TO PRODUCE A TARGET OLFACTORY PLEASANTNESS

(71) Applicant: International Business Machines Corporation, Armonk, NY (US)

(72) Inventors: Yi-Min Chee, Yorktown Heights, NY (US); Angela Schoergendorfer, New York, NY (US); Lav R. Varshney, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 453 days.

(21) Appl. No.: 13/871,689

(22) Filed: Apr. 26, 2013

(65) Prior Publication Data
US 2014/0324932 A1 Oct. 30, 2014

(51) Int. Cl.
*G01N 33/00* (2006.01)
*G06F 17/00* (2006.01)
*B60H 3/00* (2006.01)
*A61L 9/03* (2006.01)

(52) U.S. Cl.
CPC ............... *G06F 17/00* (2013.01); *A61L 9/035* (2013.01); *B60H 3/0035* (2013.01); *A61L 2209/11* (2013.01); *A61L 2209/111* (2013.01); *B60H 2003/0064* (2013.01); *G01N 33/0001* (2013.01)

(58) Field of Classification Search
CPC .......... G01N 33/0001; G01N 30/8675; G01N 33/0031; G01N 33/0098; G01N 33/02; G01N 33/12; G01N 33/14; G01N 33/146; G01N 33/46; G01N 33/497
See application file for complete search history.

(56) References Cited

U.S. PATENT DOCUMENTS

| 3,815,405 | A | * | 6/1974 | Dravnieks | .......... G01N 30/8675 |
| | | | | | 436/161 |
| 5,355,718 | A | * | 10/1994 | Mookherjee et al. | ........ 73/23.34 |
| 5,367,899 | A | * | 11/1994 | Mookherjee et al. | ........ 73/23.34 |
| 5,369,978 | A | * | 12/1994 | Mookherjee et al. | ........ 73/23.34 |
| 5,724,256 | A | | 3/1998 | Lee et al. | |
| 5,801,297 | A | * | 9/1998 | Mifsud et al. | ................ 73/23.34 |
| 6,024,783 | A | | 2/2000 | Budman | |
| 6,463,786 | B1 | * | 10/2002 | Behan | ...................... A61B 5/00 |
| | | | | | 434/236 |
| 6,672,129 | B1 | * | 1/2004 | Frederickson et al. | ........ 73/1.06 |
| 6,741,954 | B2 | * | 5/2004 | Sonnenberg | ............. A61K 8/02 |
| | | | | | 510/101 |
| 7,143,631 | B2 | * | 12/2006 | Nurcombe | ................... 73/23.34 |

(Continued)

FOREIGN PATENT DOCUMENTS

WO 00/15268 A1 3/2000
WO 00/15269 A1 3/2000

OTHER PUBLICATIONS

Joseph 'Jofish' Kaye, "Symbolic Olfactory Display," S.M. Thesis, Massachusetts Institute of Technology, May 2001, 144 pages.

(Continued)

*Primary Examiner* — David A Rogers
(74) *Attorney, Agent, or Firm* — Louis J. Percello; Ryan, Mason & Lewis, LLP

(57) ABSTRACT

An apparatus comprises a decoder and an actuator. The decoder is configured to receive a signal comprising a target olfactory pleasantness, to determine one or more combinations of odors which produce the target olfactory pleasantness, and to select a given one of the combinations of odors. The actuator is coupled to the decoder and configured to utilize the given combination of odors to produce an odor with the target olfactory pleasantness.

17 Claims, 8 Drawing Sheets

(56) References Cited

U.S. PATENT DOCUMENTS

| | | | |
|---|---|---|---|
| 7,413,550 B2* | 8/2008 | MacDonald et al. | 600/532 |
| 7,726,211 B2* | 6/2010 | Montefusco | 73/863.71 |
| 7,905,154 B2* | 3/2011 | Jones, Jr. | 73/864.81 |
| 7,971,470 B2* | 7/2011 | Broz | 73/31.03 |
| 8,826,723 B2* | 9/2014 | Henry | 73/23.34 |
| 2005/0141668 A1* | 6/2005 | Nurcombe | G01N 33/0001 378/112 |
| 2012/0143804 A1 | 6/2012 | Haddad et al. | |

OTHER PUBLICATIONS

H. Lapid et al., "Prediction Models for the Pleasantness of Binary Mixtures in Olfaction," Chem Senses, Sep. 2008, pp. 599-609, vol. 33, No. 7.

R. Haddad et al., "Predicting Odor Pleasantness with an Electronic Nose," PLoS Computational Biology, e1000740, Apr. 2010, 11 pages, vol. 6, No. 4.

* cited by examiner

DETERMINING COMBINATIONS OF ODORS TO PRODUCE A TARGET OLFACTORY PLEASANTNESS

FIELD

The field relates to signal communication and, more particular to techniques for synthesis and communication of olfactory signals.

BACKGROUND

The production of particular odors is used in a wide variety of application areas. Olfactory actuators and other hardware can be utilized to produce a particular odor in such application areas. While the space of chemicals and other odor-producing sources is large and complicated, the quality of smells is more limited. Human odor perception space is based generally on three dimensions: pleasantness, familiarity and intensity. Humans are able to perceive and recognize many different smells, but judge the quality of odors primarily on the single dimension of pleasantness.

SUMMARY

According to one embodiment of the invention, an apparatus comprises a decoder and an actuator. The decoder is configured to receive a signal comprising a target olfactory pleasantness, to determine one or more combinations of odors which produce the target olfactory pleasantness, and to select a given one of the combinations of odors. The actuator is coupled to the decoder and configured to utilize the given combination of odors to produce an odor with the target olfactory pleasantness.

According to another embodiment of the invention, a method comprises receiving a signal comprising a target olfactory pleasantness, determining one or more combinations of odors which produce the target olfactory pleasantness, selecting a given one of the combinations of odors, and communicating the given combination of odors to an actuator configured to utilize the given combination to produce an odor with the target olfactory pleasantness. The receiving, determining, selecting and communicating steps are performed by at least one processor device.

According to another embodiment of the invention, a system comprises a decoder module and an actuator module. The decoder module is configured to receive a signal comprising a target olfactory pleasantness, to determine one or more combinations of odors which produce the target olfactory pleasantness, and to select a given one of the combinations of odors. The actuator module configured to utilize the given combination of odors to produce an odor with the target olfactory pleasantness. The decoder module and the actuator module are each implemented using at least one processing device comprising a processor coupled to a memory.

These and other embodiments of the invention will become apparent from the following detailed description of illustrative embodiments thereof, which is to be read in connection with the accompanying drawings.

DETAILED DESCRIPTION

Illustrative embodiments of the invention may be described herein in the context of illustrative methods, systems and devices for the synthesis and communication of olfactory signals. However, it is to be understood that embodiments of the invention are not limited to the illustrative methods, systems and devices described but instead are more broadly applicable to other suitable methods, systems and devices.

Embodiments of the invention provide techniques for the synthesis and communication of olfactory signals based on a pleasantness dimension of the olfactory signals. Embodiments of the invention utilize pleasantness rather than the identification of a particular odor, to communicate and produce odors. Embodiments of the invention, however, may utilize the categorical delineation of particular odors to supplement identification or reproduction of an odor with a particular pleasantness.

The pleasantness of a mixture of odors may be determined from a linear combination of the pleasantness of constituent odors in the mixture, weighted by the respective intensities of the constituent odors. This linearity, however, does not imply that simple intensity scaling of individual odors can modulate their respective pleasantness.

In many application areas, the reproduction of an exact odor is not necessary. Instead, it may be sufficient to instead invoke a certain level of pleasantness with an odor. In other applications, a particular category of scents or odors with a specific level of pleasantness may be sufficient. Application areas include, by way of example, marketing, entertainment, virtual reality, product design, and warning signals. Marketing application areas include the on-site elicitation of emotions using odor pleasantness, advertising and public promotion. Entertainment application areas include various immersive forms of entertainment such as video games, cinema, theaters, etc. Virtual reality application areas used for education and training can benefit from immersive experiences which include olfactory sensory perception. Product design includes products such as culinary recipes and fragrance design. Warning signals can include, for example, natural gas leaks, emergency situations, etc.

Figure 1:
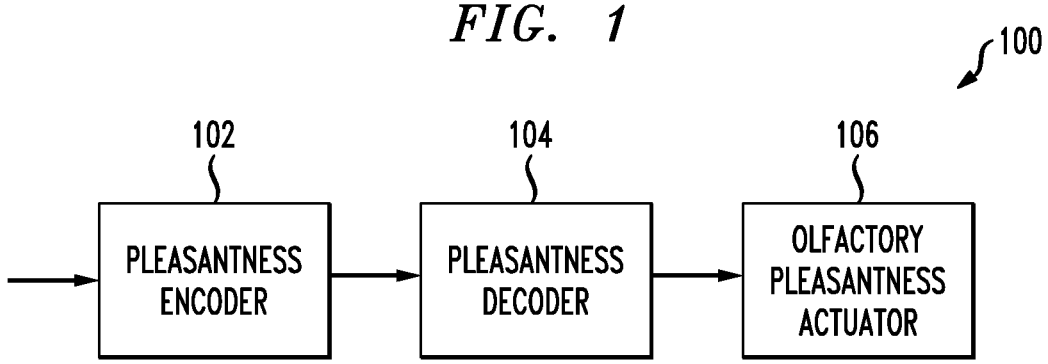
FIG. 1 illustrates an apparatus for communication and synthesis of olfactory signals, according to an embodiment of the invention.

FIG. 1 illustrates an olfactory pleasantness reproduction apparatus 100 for the communication and synthesis of olfactory signals. The olfactory pleasantness reproduction apparatus 100 comprises a pleasantness encoder 102, a pleasantness decoder 104 and an olfactory pleasantness actuator 106. Pleasantness encoder 102 is configured to receive a chemical or other odor source and encode the source for communication to the pleasantness decoder 104. The odor source may be an ambient odor at a particular location or received as input from another device. For example, the pleasantness encoder 102 may be configured to measure an olfactory pleasantness or odor at a particular location and convert this olfactory pleasantness or odor into an olfactory signal for transmission to the pleasantness decoder 104. The pleasantness encoder 102 may alternately receive an identification of a particular source odor or source odor pleasantness and convert this identification into a signal for transmission to the pleasantness decoder 104.

The pleasantness decoder 104 receives a signal from the pleasantness encoder 102. The signal comprises a target olfactory pleasantness to be reproduced. The signal may comprise a particular source odor which the pleasantness decoder 104 must convert into an olfactory pleasantness, or the signal may itself comprise the target olfactory pleasantness. In some embodiments, the target olfactory pleasantness may be one of a set of discrete pleasantness levels. The pleasantness decoder 104 may map a source odor to a given one of the discrete pleasantness levels. In some embodiments, the signal may comprise information relating to a particular scent category in addition to information relating to a target olfactory pleasantness. For example, the signal may indicate a particular olfactory pleasantness level in a scent category of a particular class of food dish or other scent categories such as floral. A codebook may be used to quantize possible pleasantness values into levels such as somewhat pleasant, pleasant, very pleasant, etc.

In some embodiments, the signal received by the pleasantness decoder 104 may be encoded. An encoding scheme may be selected and used by the pleasantness encoder 102 so as to reduce or minimize communication overhead in transmitting the signal comprising the target olfactory pleasantness to the pleasantness decoder 104. In some embodiments, an encoding scheme may be selected which reduces a number of bits required to transmit the target olfactory pleasantness.

The pleasantness decoder 104 is configured to determine combinations of odors which produce the target olfactory pleasantness. For example, a number of different combinations of odors may produce an odor with the same olfactory pleasantness, or with a same olfactory pleasantness level. The pleasantness decoder 104 selects one of the combinations of odors for communication to the olfactory pleasantness actuator 106. The olfactory pleasantness actuator 106 is configured to utilize the selected combination of odors to produce an odor with the target olfactory pleasantness. The selected combination of odors may be communicated to the olfactory pleasantness actuator 106 as a set of concentrations of constituent odors.

In some embodiments, the pleasantness decoder 104 may encode a mixture or combination of odors into an encoded pleasantness value for communication to the olfactory pleasantness actuator 106. The actuated constituents may be selected independent of the constituents of the original odor from which the pleasantness value was decoded. Thus the pleasantness decoder 104 does not need to recreate a specific odor and instead encodes a pleasantness value which evokes a target olfactory pleasantness. The encoded pleasantness value may be generated under different and multiple actuation constraints and objectives related to cost, availability, health, toxicity considerations, etc. as will be detailed below.

Figure 2:
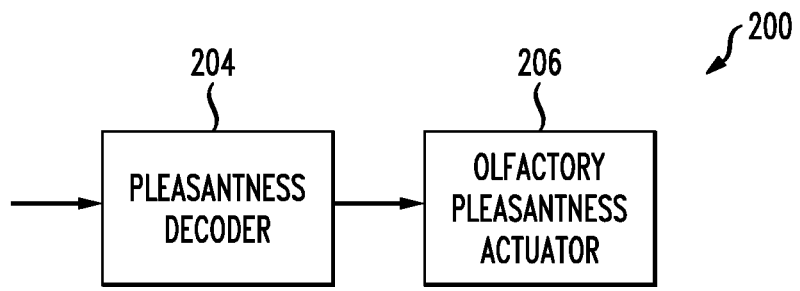
FIG. 2 illustrates another apparatus for communication and synthesis of olfactory signals, according to an embodiment of the invention.

FIG. 2 illustrates an olfactory pleasantness reproduction apparatus 200 for the communication and synthesis of olfactory signals. The olfactory pleasantness reproduction apparatus 200 comprises a pleasantness decoder 204 and an olfactory pleasantness actuator 206. The pleasantness decoder 204 and olfactory pleasantness actuator 206 are configured to perform functions similar to those described above with respect to the pleasantness decoder 104 and olfactory pleasantness actuator 106 of apparatus 100. The pleasantness decoder 204 is configured to receive a signal comprising a target olfactory pleasantness. The pleasantness decoder 204 determines combinations of odors which produce the target olfactory pleasantness and selects one of the combinations of odors for communication to the olfactory pleasantness actuator 206, which utilizes the selected combination of odors to produce an odor with the target olfactory pleasantness. The olfactory pleasantness reproduction apparatus 200 may receive the signal comprising the target olfactory pleasantness from a number of sources, including but not limited to a pleasantness encoder such as in olfactory pleasantness reproduction apparatus 100 in FIG. 1, a computer or other processing device, etc.

The olfactory pleasantness reproduction apparatus 100 in FIG. 1 may be utilized in situations in which an olfactory pleasantness at one point is to be evoked at a distant point under actuation constraints. By way of example, the olfactory pleasantness reproduction apparatus 100 may be utilized for warning signals. For example, the pleasantness encoder 102 may be configured to detect chemical sources and other odors in a fresh food compartment of a refrigerator, wherein the olfactory pleasantness actuator 106 may produce an odor with the target olfactory pleasantness outside the refrigerator to alert a user if food in the fresh food compartment has spoiled. As another example, the pleasantness encoder 102 may be configured to detect chemical sources and other odors in or around a gas tank, boiler, heater or other appliance, wherein the olfactory pleasantness actuator 106 reproduces an odor with the target olfactory pleasantness at a monitoring station.

The olfactory pleasantness reproduction apparatus 200 in FIG. 2 may be utilized for other application areas where a given olfactory pleasantness is to be evoked, rather than reproducing an olfactory pleasantness from a source location. The olfactory pleasantness reproduction apparatus 200 may be utilized in application areas such as advertisement, immersive entertainment such as virtual reality simulations, video games, cinema, etc.

While FIG. 1 illustrates an olfactory pleasantness reproduction apparatus 100 with only a single instance of a pleasantness encoder 102, pleasantness decoder 104 and olfactory pleasantness actuator 106, embodiments are not limited to this arrangement. In other embodiments an apparatus may comprise multiple instances of pleasantness encoders, pleasantness decoders and olfactory pleasantness actuators. Similarly, while FIG. 2 illustrates an olfactory pleasantness reproduction apparatus 200 with only a single instance of pleasantness decoder 204 and olfactory pleasantness actuator 206, embodiments are not limited solely to this arrangement.

Figure 3:
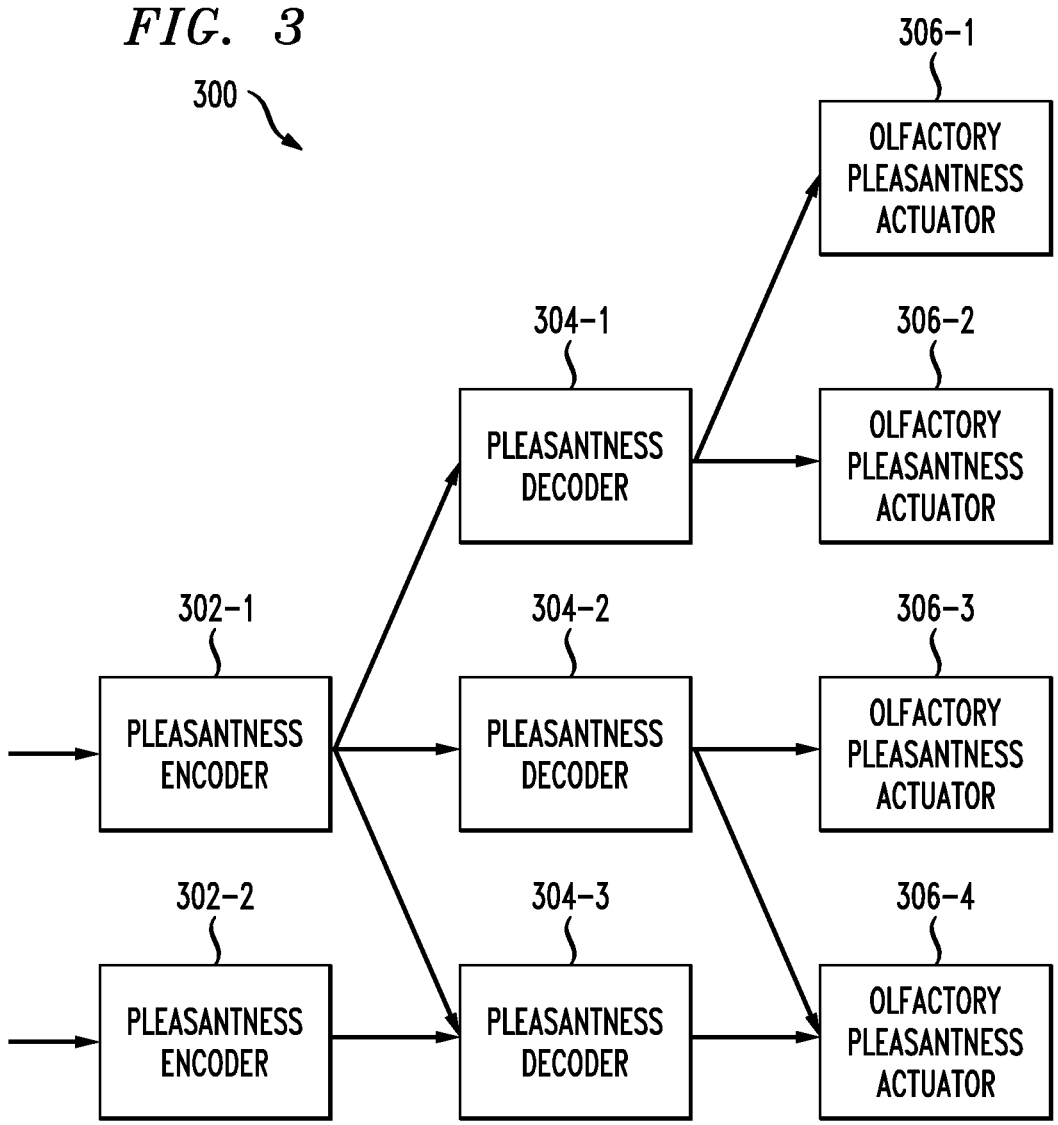
FIG. 3 illustrates another apparatus for communication and synthesis of olfactory signals, according to an embodiment of the invention.

FIG. 3 illustrates an olfactory pleasantness reproduction apparatus 300 with multiple instances of pleasantness encoders, pleasantness decoders and olfactory pleasantness actuators. Olfactory pleasantness reproduction apparatus 300 has pleasantness encoders 302-1 and 302-2. Pleasantness encoder 302-1 is coupled to pleasantness decoders 304-1, 304-2 and 304-3. Pleasantness encoder 302-2 is coupled to pleasantness decoder 304-3. Pleasantness decoder 304-1 is coupled to olfactory pleasantness actuators 306-1 and 306-2, pleasantness decoder 304-2 is coupled to olfactory pleasantness actuators 306-3 and 306-4, and pleasantness decoder 304-3 is coupled to olfactory pleasantness actuator 306-4.

The olfactory pleasantness reproduction apparatus 300 may be utilized in a wide variety of application areas. By way of example, the pleasantness encoders 302-1 and 302-2 may be configured to convert chemical sources or odors at two or more disparate locations into signals comprising a target olfactory pleasantness for transmission to the pleasantness decoders 304. The pleasantness encoders 302-1 and 302-2 may be placed near one or more appliances or structures such as gas tanks, boilers, heaters, etc. to provide warning signals. The pleasantness encoders 302-1 and 302-2 may be placed near two different appliances or structures to provide warnings for both, or may be placed near the same appliance or structure to provide a failsafe or to provide status information and warning signals of two different types for a particular appliance or structure. The olfactory pleasantness actuators 306 may be configured to produce odors in multiple monitoring stations or other locations.

The pleasantness encoders 302 can be configured to convert source odors at two or more separate locations for communication to the pleasantness decoders 304. The pleasantness decoders 304 may select combinations of odors for reproduction by the olfactory pleasantness actuators at separate locations. It is important to note that each pleasantness decoder 304 may select a different combination of odors, or two or more of the pleasantness decoders 304 may select the same combination of odors. In addition, one of the pleasantness decoders 304, such as pleasantness decoder 304-1, may select one combination of odors to transmit to olfactory pleasantness actuator 306-1 and a different combination of odors to transmit to olfactory pleasantness actuator 306-2.

As will be detailed below, the particular combinations of odors transmitted to respective ones of the olfactory pleasantness actuators 306 may be determined based at least on part on constraints specific to the respective olfactory pleasantness actuators 306. For example, olfactory pleasantness actuator 306-1 and olfactory pleasantness actuator 306-2 may have access to a different set of available constituent odors which may be used for the production of an odor with the target olfactory pleasantness. Thus, it is to be appreciated that the odor produced by an olfactory pleasantness actuator in embodiments of the invention need not be the same as a source odor. In some embodiments, the produced odor may be different than the source odor, or more than two odors may be produced, where one or both are different than the source odor.

It is important to note that FIG. 3 illustrates only one possible configuration of multiple pleasantness encoders 302, pleasantness decoders 304 and olfactory pleasantness actuators 306. Embodiments of the invention may be configured with any number of arbitrary topologies of pleasantness encoders, pleasantness decoders and olfactory pleasantness actuators. A single pleasantness encoder coupled to multiple pleasantness decoders may be considered a multicast system. A given olfactory pleasantness actuator shared among two or more pleasantness decoders may be considered a multiple access system.

In some embodiments, each pleasantness encoder is coupled to at least one pleasantness decoder and each pleasantness decoder is coupled to at least one olfactory pleasantness actuator. While FIG. 3 shows an olfactory pleasantness reproduction apparatus 300 in which there are more olfactory pleasantness actuators 306 than pleasantness decoders 304 and more pleasantness decoders 304 than pleasantness encoders 302, embodiments of the invention are not so limited. For example, a system in some embodiments may have a plurality of pleasantness encoders and a plurality of olfactory pleasantness actuators coupled to a single pleasantness decoder. As another example, an apparatus may comprise one or more pleasantness decoders which are not coupled to a pleasantness encoder. One skilled in the art will readily appreciate that various other examples are possible.

Pleasantness decoders in embodiments of the invention may utilize simplex plots to determine combinations of odors with a target olfactory pleasantness. As discussed above the pleasantness of a mixture or combination of odors may be determined at least in part from a linear combination of the pleasantness of constituent odors in the mixture or combination, weighted by their respective intensities. The signal received by the pleasantness decoder may comprise a set of coordinates on one or more simplex plots of odors, where odors on the simplex plot are associated with respective olfactory pleasantness values. The set of coordinates in the signal may alternately comprise a partition of a simplex plot. A sequence of points on a simplex plot is a possible time-varying strategy for the communication and generation of olfactory pleasantness. The corner points of a simplex may be pure compounds or mixtures of two or more compounds.

Figure 4:
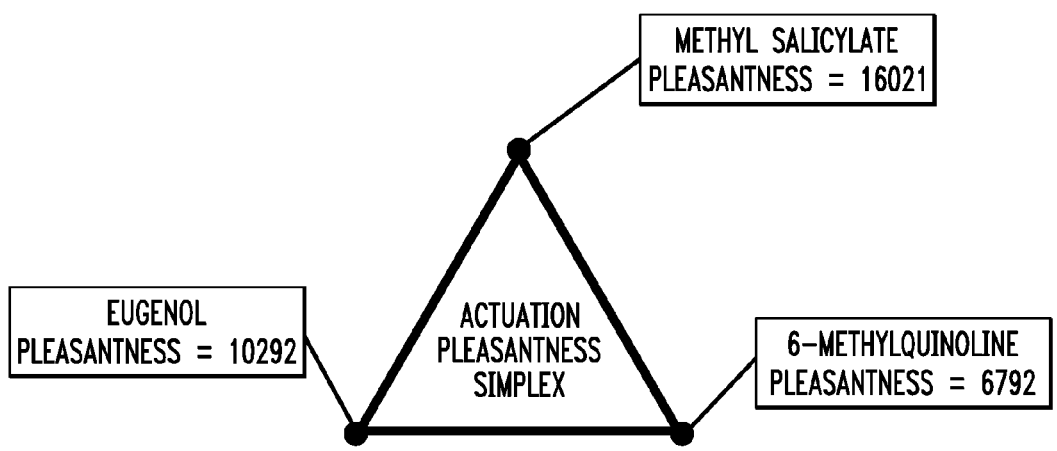
FIG. 4 illustrates an actuation pleasantness simplex plot, according to an embodiment of the invention.
Figure 5:
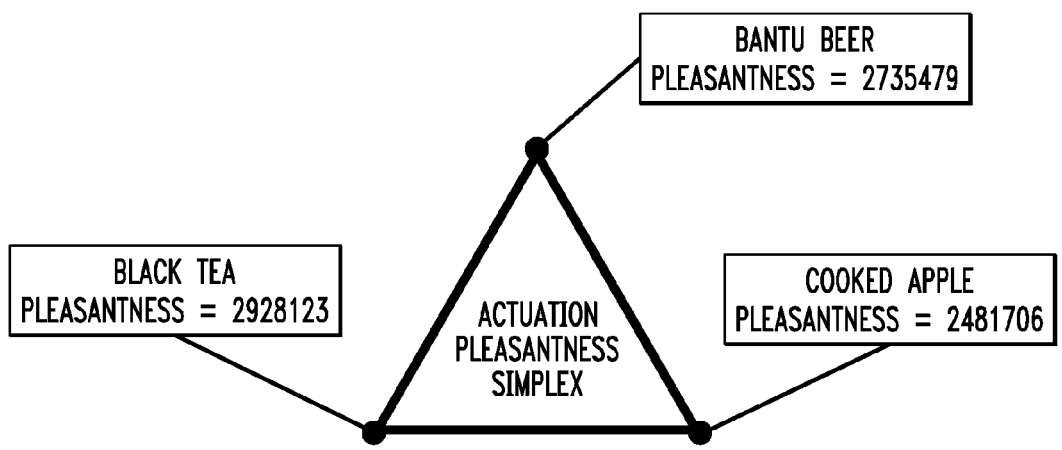
FIG. 5 illustrates another actuation pleasantness simplex plot, according to an embodiment of the invention.

FIGS. 4 and 5 illustrate actuation pleasantness simplex plots. FIG. 4 illustrates a first actuation pleasantness simplex, wherein the corners of the simplex are eugenol, methyl salicylate and 6-methylquinoline with respective pleasantness values of 10,292, 16,021 and 6,792. FIG. 5 illustrates a second actuation pleasantness simplex, wherein the corners of the simplex are black tea, Bantu beer and cooked apple with respective pleasantness values of 2,928,123, 2,735,479 and 2,481,706. An olfactory signal may specify particular coordinates on an actuation pleasantness simplex which correspond to a mixture of eugenol, methyl salicylate and 6-methylquinoline or a mixture of black tea, Bantu beer and cooked apple which produce a target olfactory pleasantness.

While FIGS. 4 and 5 illustrate actuation pleasantness simplexes with definite corner pleasantness values, in some embodiments the pleasantness values associated with corners of a simplex plot may be uncertain. Each corner may have a pleasantness value and a corresponding certainty, such that a pleasantness decoder takes into account the respective certainties of pleasantness values associated with constituent odors when selecting a combination of odors on the simplex plot. A combination of odors may be selected which minimizes the uncertainty in target olfactory pleasantness. Various other factors may be used to select a combination of odors, which will be described in further detail below. In addition, while FIGS. 4 and 5 illustrate 3-dimensional simplex plots with three corners, embodiments of the invention may utilize one or more n-dimensional simplex plots with more or less than three corners.

Figure 6:
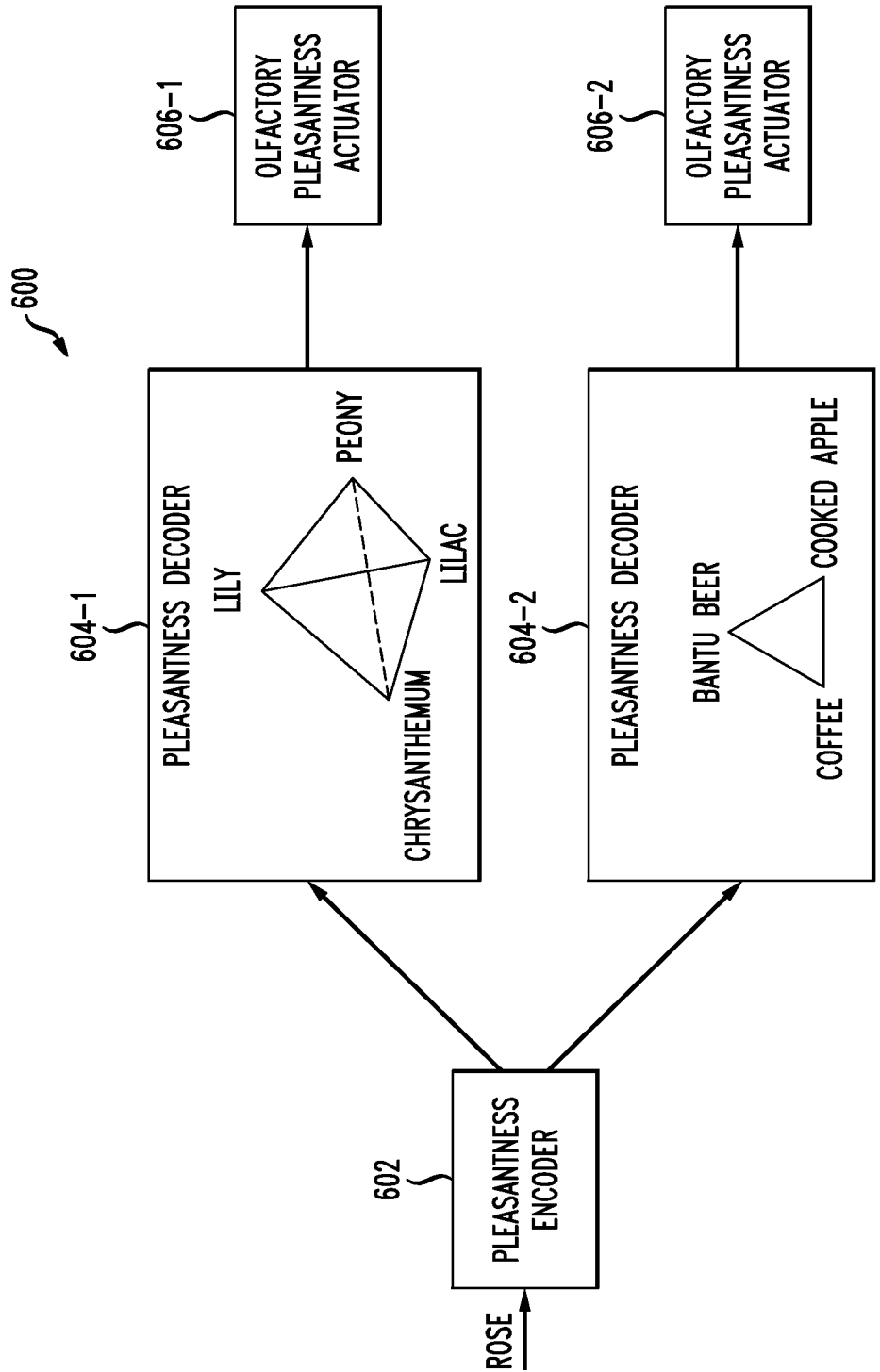
FIG. 6 illustrates a system for communication and synthesis of olfactory signals using simplex plots, according to an embodiment of the invention.

FIG. 6 illustrates an olfactory pleasantness reproduction system 600 for the communication and synthesis of olfactory signals utilizing simplex plots. A pleasantness encoder 602 receives a source odor of rose, and transmits the source odor as a signal comprising a target olfactory pleasantness to pleasantness decoders 604-1 and 604-2. Pleasantness decoder 604-1 utilizes a 4-dimensional actuation pleasantness simplex with constituent odors lily, peony, lilac and chrysanthemum. Pleasantness decoder 604-2 utilizes a 3-dimensional actuation pleasantness simplex with constituent odors Bantu beer, cooked apple and coffee. The pleasantness decoder 604-1 selects a combination of constituent odors lily, peony, lilac and chrysanthemum which produces an odor with an olfactory pleasantness similar to or substantially equal to the olfactory pleasantness of the source odor rose. The pleasantness decoder 604-2 selects a combination of constituent odors Bantu beer, cooked apple and coffee which produces an odor with an olfactory pleasantness similar to or substantially equal to the olfactory pleasantness of the source odor rose.

As described above, the pleasantness decoders 604 may select a combination of odors with a same pleasantness level as that of rose, where the pleasantness level is one of a number of discrete pleasantness levels. Thresholds may be used to determine whether combinations of constituent odors have an olfactory pleasantness similar to or substantially equal to that of the source odor. Such thresholds may take into account the uncertainties associated with pleasantness of constituent odors as discussed above.

The olfactory pleasantness actuators 606-1 and 606-2 are configured to utilize the combinations of odors selected in the pleasantness decoders 604-1 and 604-2, respectively, to produce odors with the target olfactory pleasantness level. The actuation pleasantness simplexes used in the pleasantness decoders 604-1 and 604-2 may be determined based at least in part on respective sets of available constituent odors in the olfactory pleasantness actuators 606-1 and 606-2 coupled to the pleasantness decoders 604-1 and 604-2.

It is important to note that in some embodiments, actuation pleasantness simplexes may be used in combination with feedback from electronic noses and other hardware, or inference models developed based on experimental pleasantness responses from humans.

Pleasantness decoders in embodiments of the invention, as described above, select a combination of odors for transmission of a target olfactory pleasantness to olfactory pleasantness actuators. Given a space of available constituent odors, there may be multiple combinations of odors which produce a target olfactory pleasantness. Pleasantness decoders in embodiments of the invention may make the selection of a particular combination so as to achieve a wide variety of objectives.

Figure 7:
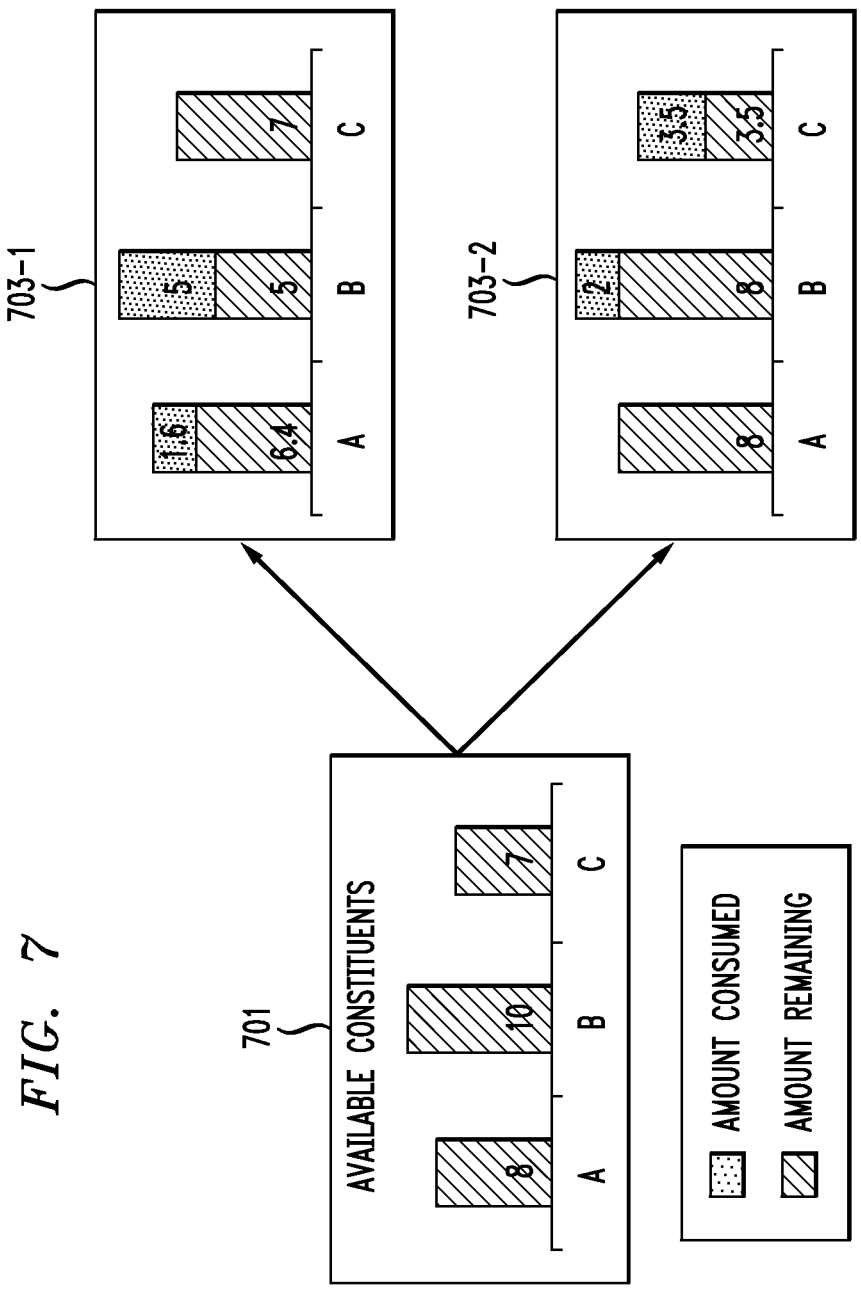
FIG. 7 illustrates an analysis of constituent availability, according to an embodiment of the invention.

One objective is to optimize the lifetime of a system by using the constituent odors in a balanced manner. A particular system may be subject to a time-varying source distribution or generative process, wherein the target olfactory pleasantness to be achieved changes dynamically. Given available amounts of constituents, a pleasantness decoder may determine several combinations which achieve the target olfactory pleasantness. FIG. 7 illustrates an analysis of constituent availability. Given a set 701 of available constituents A, B and C, a pleasantness decoder may determine that there are two combinations 703-1 and 703-2 of constituent odors A, B and C which produce a target olfactory pleasantness. The first combination 703-1 uses 1.6 units of constituent A and 5 units of constituent B. The second combination 703-2 uses 2 units of constituent B and 3.5 units of constituent C.

To maximize the lifetime of a system, the pleasantness decoder may select the combination which minimizes a total or relative amount of resources consumed or alternatively select the option which minimizes variability of the remaining amounts of available constituents. In some embodiments, the pleasantness decoder may achieve a tradeoff between minimizing total or relative amount of resources consumed and minimizing the variability in remaining constituents. In the example of FIG. 7, the pleasantness decoder may select combination 703-2 to minimize the total amount of resources consumed or select combination 703-1 to minimize variability between remaining constituents.

Given an olfactory pleasantness actuator with a set of n different constituents, a solution to achieve a target pleasantness may be given by $\{a, i, b, j\}$, where a denotes the units of constituent i and b denotes the units of constituent j. There will be at most $$\frac{n!}{2*(n-2)!}$$

possible solutions. One approach is to select a combination of constituents which minimizes a+b. Let $u_1 \ldots u_n$ denote the remaining number of units for each compound for a given unit definition. Another approach is to select the solution which consumes the minimum fraction of remaining compounds according to $$\left(\frac{a}{u_i} + \frac{b}{u_j}\right)/2 \text{ or } \max\left(\frac{a}{u_i}, \frac{b}{u_j}\right).$$

As discussed above, other approaches may select combinations of odors so as to reduce or minimize the variance of the remaining amounts across the set of available constituents.

In some embodiments, a probability distribution may be utilized to select combinations of available constituents. The probability distribution may indicate what is likely to be generated over time to optimize a sequence of actions by reducing or minimizing the expected value of the approaches discussed above. For example, a probability distribution may indicate that a first constituent is used to produce a relatively large proportion of target olfactory pleasantness levels while a second constituent is used to produce a relatively small proportion of target olfactory pleasantness levels. Thus, if a particular target olfactory pleasantness level may be achieved using two combinations using the first and second constituents, respectively, the pleasantness decoder may select the combination which uses the second constituent so as to maximize the lifetime of the system. If the stochastic process is Markov, dynamic programming may be utilized to select the odor combinations. It is important to note that embodiments of the invention may also utilize combinations of two or more of the above approaches to maximize the lifetime of the system.

Figure 8:
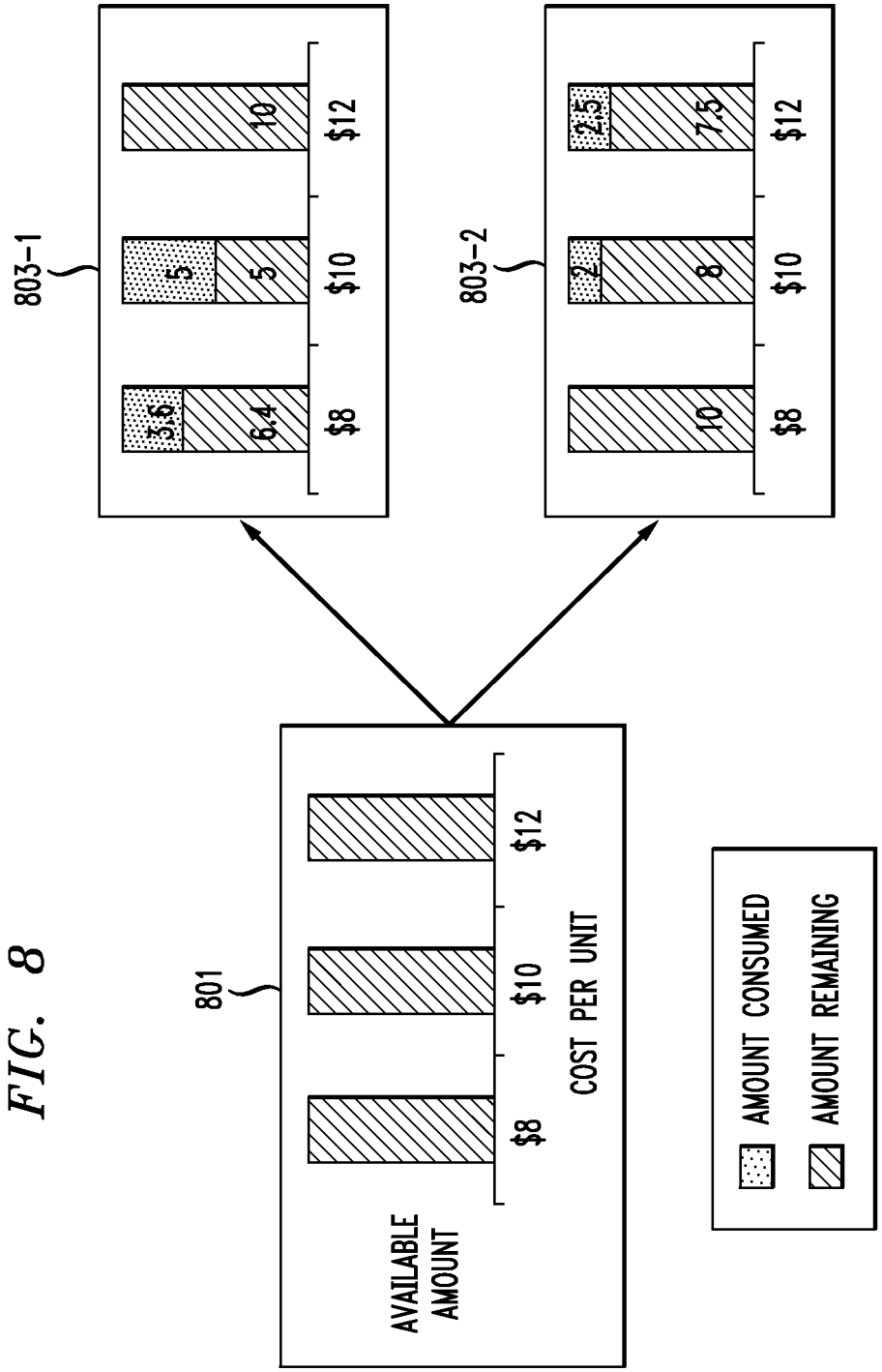
FIG. 8 illustrates an analysis of constituent cost, according to an embodiment of the invention.

Another objective is to reduce, minimize or otherwise optimize the actuation cost of the selected combination of constituent odors. Each constituent odor may have an associated monetary cost. A combination of constituent odors may be selected which reduces or minimizes the cost of producing the target olfactory pleasantness. FIG. 8 illustrates an analysis of constituent cost. A set 801 of available constituents have associated costs of $8 per unit, $10 per unit and $12 per unit. A first combination of constituents 803-1 utilizes 3.6 units of the $8 per unit constituent and 5 units of the $10 per unit constituent for a total cost of $78.80. A second combination of constituents 803-2 utilizes 2 units of the $10 per unit constituent and 2.5 units of the $12 per unit constituent for a total cost of $55.

Again, given an olfactory pleasantness actuator with a set of n different constituent odors, the solution to achieve a target olfactory pleasantness may be given by $\{a, i, b, j\}$, where a denotes the units of constituent i and b denotes the units of constituent j. Let $p_1 \ldots p_n$ denote the per unit cost of each constituent odor for a particular unit definition. There will be at most $$\frac{n!}{2*(n-2)!}$$

possible solutions. One approach is to simply choose the solution with the minimum cost given by $(a*p_i)+(b*p_j)$. If two or more combinations have the same cost, one or more of the approaches described above with respect to the objective of maximizing the lifetime of the system may be used. For example, the pleasantness decoder may select between two combinations with the same cost by selecting the combination which uses the least total number of units (a+b) or the combination which reduces variability among remaining constituents. Similar to the objective of maximizing the lifetime of the system, probability distributions may be used for achieving the objective of reducing, minimizing or otherwise reducing the actuation cost in the system.

As described above, another objective may be to reduce the cost of signaling the target olfactory pleasantness. In certain applications, the cost of signaling may outweigh the cost of actuation or be a significant factor which should be taken into account. Probability distributions may be used to detet nine a communication-efficient encoding or compression scheme which reduces communication overhead for transmitting olfactory signals. In certain systems and applications, there may be multiple actuators, each of which has a different set of available constituent odors. Each olfactory pleasantness actuator may use a different combination of odors to achieve a target olfactory pleasantness. Thus, the pleasantness decoders may multicast a target olfactory pleasantness to the olfactory pleasantness actuators, such that each actuator may select the combination of odors which achieves a particular objective or objectives for the system. Alternately, the pleasantness decoders may unicast combinations to respective ones of the olfactory pleasantness actuators, or use some combination of unicasting and multicasting to transmit the target olfactory pleasantness and/or selected combinations to a set of olfactory pleasantness actuators.

The objective of reducing the cost of signaling may be achieved by solving a data compression equation such as $\min_{p(y|x):E[d(y,x)]<D} I(X:Y)$ where I is mutual information, D is a distortion constraint, and d is a distortion measure that measures olfactory pleasantness. The goal is to find the coding scheme $p(y|x)$ that partitions an actuation simplex optimally for this objective, when the original olfactory signal to communicate is pleasantness x and the reproduction is y.

Embodiments of the invention may also utilize two or more of the above-described objectives and approaches for a particular system. In some embodiments, objectives may be ranked hierarchically in order of importance. Optimizing may be done in the order of the hierarchy, using the next level of the hierarchy for tiebreakers. In other embodiments, each objective may be given a particular weight and the selected combination is determined using the weighted combinations for two or more objectives. For example, some embodiments may use weighted combinations to consider the objectives of minimizing cost and balanced consumption of constituent odors. The objective of reducing the cost of signaling may be considered separate from other objectives in some embodiments of the invention, as communication overhead influences possible actuation strategies in a different manner than maximizing lifetime or reducing cost.

Figure 9:
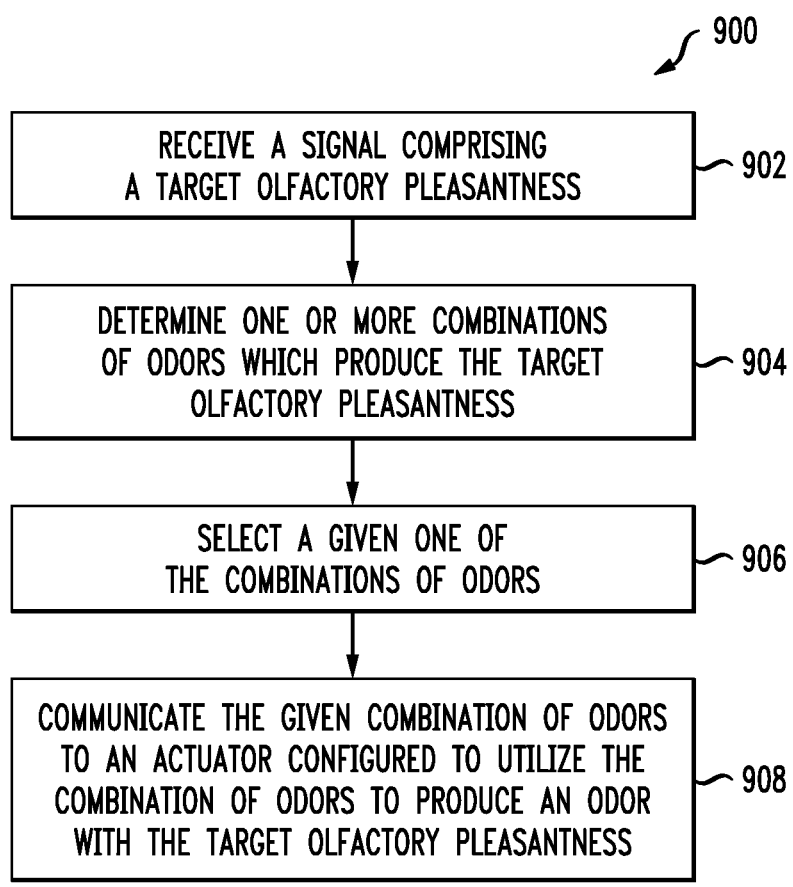
FIG. 9 illustrates a methodology for communication and synthesis of olfactory signals, according to an embodiment of the invention.

FIG. 9 illustrates a methodology 900 for the communication and synthesis of olfactory signals. The methodology begins with step 902, receiving a signal comprising a target olfactory pleasantness. Next, one or more combinations of odors which produce the target olfactory pleasantness are determined 904. A given one of the combinations of odors is selected 906, and the given combination of odors is communicated 908 to an actuator. The actuator is configured to utilize the combination of odors to produce an odor with the target olfactory pleasantness.

Figure 10:
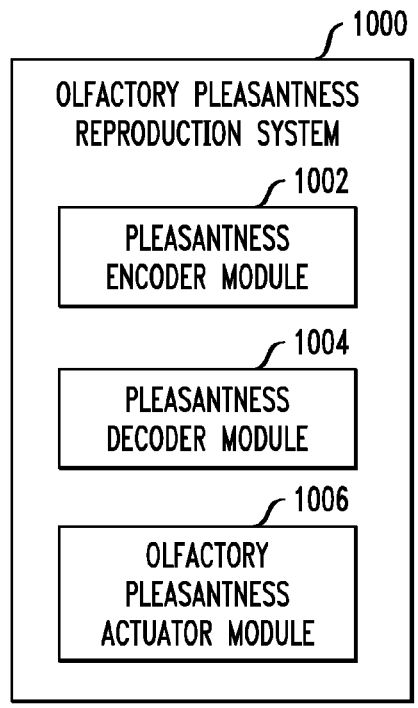
FIG. 10 illustrates an olfactory pleasantness reproduction system, according to an embodiment of the invention.

FIG. 10 illustrates an olfactory pleasantness reproduction system 1000. The olfactory pleasantness reproduction system 1000 comprises a pleasantness encoder module 1002, a pleasantness decoder module 1004 and an olfactory pleasantness actuator module 1006. The pleasantness encoder module 1002, pleasantness decoder module 1004 and olfactory pleasantness actuator module 1006 are configured to perform functionality described above with respect to pleasantness encoders, pleasantness decoders and olfactory pleasantness actuators, respectively.

As will be appreciated by one skilled in the art, aspects of the present invention may be embodied as a system, apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be but are not limited to, for example, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Referring again to FIGS. 1-10, the diagrams in the figures illustrate the architecture, functionality, and operation of possible implementations of systems, methods and computer program products according to various embodiments of the present invention. In this regard, each block in a flowchart or a block diagram may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagram and/or flowchart illustration, and combinations of blocks in the block diagram and/or flowchart illustration, can be implemented by special purpose hardware-based systems that perform the specified functions or acts, or combinations of special purpose hardware and computer instructions.

Accordingly, techniques of the invention, for example, as depicted in FIGS. 1-10, can also include, as described herein, providing a system, wherein the system includes distinct modules (e.g., modules comprising software, hardware or software and hardware).

Figure 11:
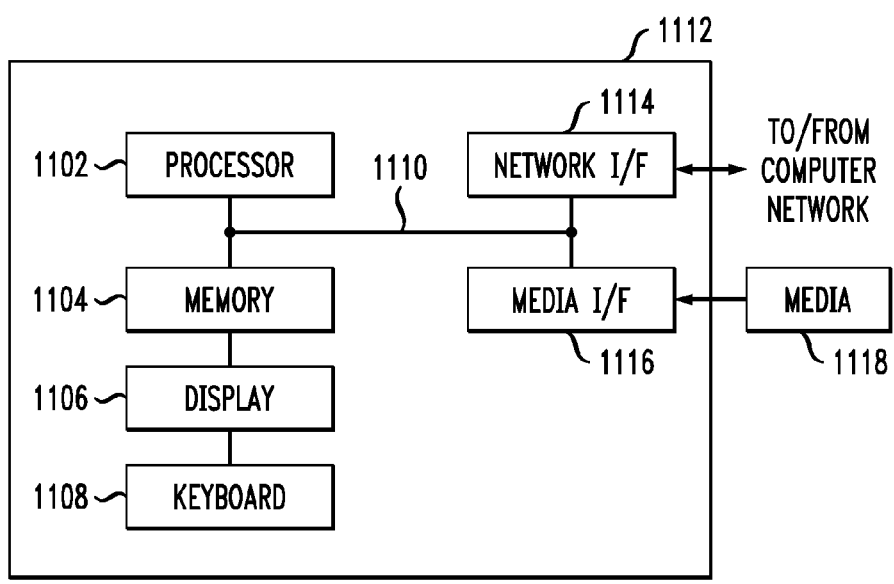
FIG. 11 illustrates a computing device in accordance with which one or more components/steps of techniques of the invention may be implemented, according to an embodiment of the invention.

One or more embodiments can make use of software running on a general purpose computer or workstation. With reference to FIG. 11, such an implementation may employ, for example, a processor 1102, a memory 1104, and an input/output interface formed, for example, by a display 1106 and a keyboard 1108. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to optionally include, for example, one or more mechanisms for inputting data to the processing unit (for example, keyboard or mouse), and one or more mechanisms for providing results associated with the processing unit (for example, display or printer).

The processor 1102, memory 1104, and input/output interface such as a display 1106 and keyboard 1108 can be interconnected, for example, via bus 1110 as part of data processing unit 1112. Suitable interconnections, for example, via bus 1110, can also be provided to a network interface 1114, such as a network card, which can be provided to interface with a computer network, and to a media interface 1116, such as a diskette or CD-ROM drive, which can be provided to interface with media 1118.

A data processing system suitable for storing and/or executing program code can include at least one processor 1102 coupled directly or indirectly to memory elements 1104 through a system bus 1110. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboard 1108 for making data entries; display 1106 for viewing data; a pointing device for selecting data; and the like) can be coupled to the system either directly (such as via bus 1110) or through intervening I/O controllers (omitted for clarity).

Network adapters such as a network interface 1114 may also be coupled to the system to enable the data processing system to become coupled to other data processing systems or remote printers or storage devices through intervening private or public networks. Modems, cable modem and Ethernet cards are just a few of the currently available types of network adapters.

As used herein, a "server" includes a physical data processing system (for example, system 1112 as shown in FIG. 11) running a server program. It will be understood that such a physical server may or may not include a display and keyboard. Further, it is to be understood that components may be implemented on one server or on more than one server.

It will be appreciated and should be understood that the exemplary embodiments of the invention described above can be implemented in a number of different fashions. Given the teachings of the invention provided herein, one of ordinary skill in the related art will be able to contemplate other implementations of the invention. Indeed, although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. An apparatus comprising:
    at least one processing device comprising a processor coupled to a memory;
    the at least one processing device being configured:
        to receive a signal comprising a target olfactory pleasantness;
        to determine one or more combinations of odors which produce the target olfactory pleasantness;
        to select a given one of the combinations of odors; and
        to utilize the given combination of odors to select amounts of respective ones of two or more available constituent odors such that the selected amounts of the available constituent odors produce a given odor with the target olfactory pleasantness;
    wherein the target olfactory pleasantness comprises a value indicative of a quality of the given odor in a defined space of odors.

2. The apparatus of claim 1, wherein the at least one processing device is further configured to convert a source odor into the signal.

3. The apparatus of claim 2, wherein the given odor and the source odor are different from one other.

4. The apparatus of claim 2, wherein the at least one processing device is further configured to select a given encoding scheme to convert the source odor into the signal, the given encoding scheme being selected based at least in part on a number of bits required to send the signal.

5. The apparatus of claim 1, wherein the given combination of odors comprises a set of constituent odors, each of the constituent odors having an olfactory pleasantness value indicative of a quality of that constituent odor in the defined space of odors, and wherein an olfactory pleasantness value of the given combination of odors comprises a linear combination of the olfactory pleasantness values of the constituent odors in the set.

6. The apparatus of claim 1, wherein the at least one processing device is further configured to map the value of the target olfactory pleasantness to a given one of a set of discrete pleasantness levels.

7. The apparatus of claim 1, wherein the at least one processing device is further configured to determine combinations of odors using a set of available constituent odor resources.

8. The apparatus of claim 7, wherein the at least one processing device is further configured to select the given combination of odors based at least in part on a total amount of constituent odor resources in the one or more combinations of odors.

9. The apparatus of claim 7, wherein the at least one processing device is further configured to select the given combination of odors based at least in part on a current availability of constituent odor resources.

10. The apparatus of claim 7, wherein the at least one processing device is further configured to select the given combination of odors based at least in part on a total cost of constituent odor resources in the one or more combinations of odors, wherein each of the available constituent odor resources has an associated cost.

11. The apparatus of claim 7, wherein the at least one processing device is further configured to select the given combination of odors based at least in part on two or more of:
    a total amount of constituent odor resources in the one or more combinations of odors;
    a current availability of constituent odor resources; and
    a total cost of constituent odor resources in the one or more combinations of odors, wherein each of the available constituent odor resources has an associated cost.

12. The apparatus of claim 1, wherein the signal comprises a set of coordinates on a simplex plot of odors and wherein odors on the simplex plot are associated with respective olfactory pleasantness values.

13. The apparatus of claim 12, wherein the set of coordinates comprises a partition of the simplex plot.

14. The apparatus of claim 12, wherein the olfactory pleasantness values associated with one or more corners of the simplex plot have respective certainties associated therewith, and wherein the at least one processing device is further configured to select the given combination of odors based at least in part on the respective certainties of constituent odors on the simplex plot.

15. The apparatus of claim 1, wherein the signal further comprises a scent category and wherein the at least one processing device is further configured to determine one or more combinations of odors which produce the target olfactory pleasantness in the scent category.

16. The apparatus of claim 1, wherein the at least one processing device is further configured:
    to select a first combination of odors based on a first store of constituent odors available for producing the given odor with the target olfactory pleasantness at a first location; and
    to select a second combination of odors different than the first combination of odors based on a second store of constituent odors available for producing the given odor with the target olfactory pleasantness at a second location different than the first location.

17. An article of manufacture comprising a processor readable storage medium for storing processor readable program code which, when executed, causes a processing device to:
    receive a signal comprising a target olfactory pleasantness;
    determine one or more combinations of odors which produce the target olfactory pleasantness;
    select a given one of the combinations of odors; and
    utilize the given combination of odors to select amounts of respective ones of two or more available constituent odors such that the selected amounts of the available constituent odors produce a given odor with the target olfactory pleasantness;
    wherein the target olfactory pleasantness comprises a value indicative of a quality of the given odor in a defined space of odors.

* * * * *